(12) United States Patent
Ramalingam

(10) Patent No.: US 12,180,150 B2
(45) Date of Patent: Dec. 31, 2024

(54) OLIGOMERIC MATERIALS FOR UV BLOCKING APPLICATIONS AND METHODS THEREOF

(71) Applicant: Agency for Science, Technology and Research, Singapore (SG)

(72) Inventor: Balamurugan Ramalingam, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 342 days.

(21) Appl. No.: 17/433,176

(22) PCT Filed: Feb. 19, 2020

(86) PCT No.: PCT/SG2020/050082
§ 371 (c)(1),
(2) Date: Aug. 23, 2021

(87) PCT Pub. No.: WO2020/176036
PCT Pub. Date: Sep. 3, 2020

(65) Prior Publication Data
US 2022/0185758 A1     Jun. 16, 2022

(30) Foreign Application Priority Data

Feb. 25, 2019 (SG) .......................... 10201901605U

(51) Int. Cl.
| | | |
|---|---|---|
| *C07C 49/255* | (2006.01) | |
| *C07C 49/753* | (2006.01) | |
| *C08G 61/02* | (2006.01) | |
| *C08K 5/132* | (2006.01) | |
| *C08L 25/06* | (2006.01) | |
| *C08L 27/06* | (2006.01) | |
| *C12P 7/26* | (2006.01) | |

(52) U.S. Cl.
CPC .......... *C07C 49/255* (2013.01); *C07C 49/753* (2013.01); *C08G 61/02* (2013.01); *C08K 5/132* (2013.01); *C08L 25/06* (2013.01); *C08L 27/06* (2013.01); *C12P 7/26* (2013.01); *C07C 2601/06* (2017.05); *C07C 2601/08* (2017.05); *C07C 2601/14* (2017.05); *C08G 2261/11* (2013.01); *C08G 2261/142* (2013.01); *C08G 2261/1422* (2013.01); *C08G 2261/1424* (2013.01); *C08G 2261/226* (2013.01); *C08G 2261/228* (2013.01); *C08G 2261/342* (2013.01); *C08G 2261/43* (2013.01); *C08G 2261/594* (2013.01); *C08G 2261/93* (2013.01)

(58) Field of Classification Search
CPC . C07C 49/255; C07C 49/753; C07C 2601/08; C07C 2601/14; C07C 2601/06; C08G 61/02; C08G 2261/11; C08G 2261/1422; C08G 2261/1424; C08G 2261/226; C08G 2261/228; C08G 2261/342; C08G 2261/594; C08G 2261/142; C08G 2261/43; C08G 2261/93; C08K 5/132; C08L 25/06; C08L 27/06; C12P 7/26
See application file for complete search history.

(56) References Cited

U.S. PATENT DOCUMENTS

2006/0235116 A1   10/2006   Lazzari et al.
2007/0060644 A1   3/2007    Jagt et al.

FOREIGN PATENT DOCUMENTS

| CN | 103214359 B | 5/2015 |
| IN | 0106CHE2013 | 5/2016 |
| WO | WO 2014/116716 | * 7/2014 |

OTHER PUBLICATIONS

Machine English translation of CN 103214359, Guo et al., Jul. 2013.*
International Search Report for PCT/SG2020/050082, mailed Jul. 1, 2020, 6 pages.
Su, J. et al., "Laccase: a green catalyst for the biosynthesis of poly-phenols", Critical Reviews in Biotechnology, 2018, vol. 38, No. 2, 294-307.
Sun, X. et al. "Laccase-Catalyzed Oxidative Polymerization of Phenolic Compounds", Applied Biochemistry and Biotechnology volume, Aug. 31, 2013, vol. 171, pp. 1673-1680.
Written Opinion of the International Searching Authority for PCT/SG2020/050082, mailed Jul. 1, 2020, 5 pages.
Mouterde, Louis M. M. et al., "Chemoenzymatic Total Synthesis of a Naturally Occurring (5-5')/(8'-O-4") Dehydrotrimer of Ferulic Acid", Eur. J. Org. Chem. 2013, 173-179.

* cited by examiner

*Primary Examiner* — Patrick D Niland
(74) *Attorney, Agent, or Firm* — McNeill PLLC

(57) ABSTRACT

The present invention describes an oligomer for use as a UV stabiliser. In particular, the oligomer is suitable for use as a UV stabiliser in a polymer matrix. The present invention also describes a method of forming said oligomer. The method of forming said oligomer comprises a polymerising step, wherein the polymerising step comprises forming a C—C bond on the hydroxyphenyl ring of a monomer. In preferred embodiments, the oligomer is formed from polymerizing bio-derived monomer such as curcumin, its hydrogenated analogue, and an aldol condensation product of cyclic ketone and vanillin.

20 Claims, 11 Drawing Sheets

90 °C for 3 days 500 mg UV stabilizer embedded PS in 10 mL of food simulant

DHBP
Uvinul 3000 (BASF)

DHOBP
Uvinul 3008 (BASF)

BTAC

Uvinul 3030 (BASF)

OLIGOMERIC MATERIALS FOR UV BLOCKING APPLICATIONS AND METHODS THEREOF

CROSS-REFERENCE TO RELATED APPLICATIONS

This application is a national stage application of International Application No. PCT/SG2020/050082 filed Feb. 19, 2020, which claims the benefit of priority of Singapore patent application Ser. No. 10/201,901605U filed Feb. 25, 2019, each of which is incorporated by reference herein in its entirety for any purpose.

FIELD

The present invention describes an oligomer for use as a UV stabiliser. The present invention also describes a method of forming said oligomer.

BACKGROUND

UV absorbers/stabilizers are blended with polymers or plastics during formulation in order to protect them from sunlight and prevent them from deterioration of mechanical properties, loss of gloss and impact strength, elongation, surface cracks and discoloration. The UV stabilisers are often added at around 2-5% weight ratio. Synthetic small organic compounds (SOCs) such as benzophenones, benzotriazoles, triazines, cyanoacrylates are commonly used as additives for UV protection. However, these small organic compounds (SOCs) are known to gradually leach from the polymer matrix to food or the atmosphere, causing long term health and environmental issues. For example, benzotriazole UV stabilizers have been shown to exhibit potent activities as human aryl hydrocarbon receptor ligands (130 nM-5 µM). A further separate study had also concluded that benzophenone UV-photoinitiators used in food packaging have potential human exposure and health risk considerations.

Further, due to increasing public awareness, legal restrictions, environmental concerns and interest to overcome limitations in conventional chemical methods, current research in the chemical industries is directed to other small molecules. This drive in research is due to the market size of this business. For example, the food packaging market rank 5th among the plastic industries based on net revenue, of which UV stabilisers plays an important part. The global UV stabiliser market is about USD 1.41 billion in 2015 and is estimated to be about USD1.51 billion by 2020.

However, thus far no desirable results is obtained from these researches.

Another research direction is to increase the molecule weights of these UV stabilisers to reduce the leaching rates. However, the problem with this concept is that high molecular weight (>15 000 Da) UV stabilisers have dispersion issues, and hence makes them unfavourable for incorporation into the plastic formulation. Further, molecules with large molecular weights are by nature larger, and thus make them more susceptible to UV degradation. This defeats the purpose of using them as UV stabilisers.

Accordingly, there is a need to overcome or at least ameliorate one or more of the above mentioned difficulties.

SUMMARY

Without wanting to be bound by theory, the inventors postulated that the stability and leaching rate of UV stabilisers can be improved by controlling the molecular weight of the UV stabilisers. However, in contrast to traditional methods, the inventors believed that the increase in molecular weight of the UV stabilisers should be performed by a direct carbon-carbon bond formation instead of amide or ester groups. It is postulated that the stronger C—C bond will make the UV stabiliser less prone to degradation and accordingly, can also improve its stability. By also forming the UV stabiliser as an oligomer, the diffusion of the UV stabiliser out of the plastic or polymers is also reduced. Further, controlling the size of the oligomer ensures that the dispersibility of the UV stabiliser in the plastic formulation is not adversely affected. A low toxicity (from the leached compounds if any) is also expected as the oligomers are based on natural products.

In an aspect, the present invention provides an oligomer of Formula (I):

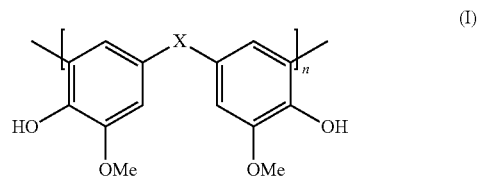

wherein X is selected from a heteroatom, $C_1$-$C_8$ acyclic, cyclic or heterocyclic linker; and n is an integer selected from 2 to 15.

In some embodiments, X is a $C_4$-$C_8$ acyclic, cyclic or heterocyclic linker.

In some embodiment, X is selected from

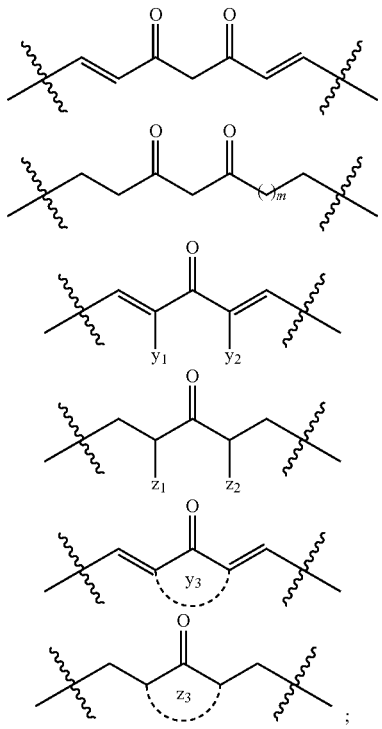

wherein m is an integer selected from 0 to 5;
$Y_1$, $Y_2$, $Z_1$ and $Z_2$ are independently $C_0$-$C_5$ alkyl; and
$Y_3$ and $Z_3$ are independently $C_4$-$C_6$ cycloalkyl.

In some embodiments, X is selected from

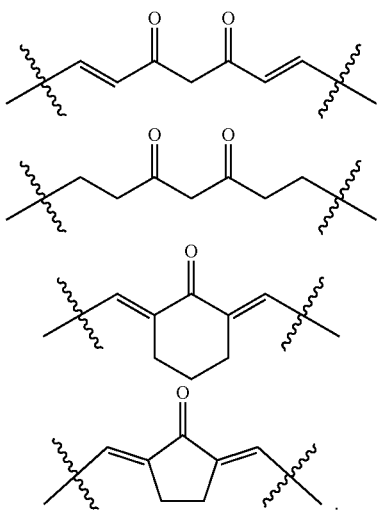

In some embodiments, n is an integer selected from 3 to 8.

In some embodiments, the oligomer of Formula (I) has an average molecular weight of about 1000 Da to about 3000 Da.

In some embodiments, the oligomer of Formula (I) has a UV absorption within the range of about 200 nm to about 500 nm.

In some embodiments, the oligomer of Formula (I) has a molar extinction coefficient of more than 30,000 $M^{-1}$ $cm^{-1}$.

In another aspect, the present invention provides a method of forming an oligomer, the method including the step of:
a) providing a monomer of Formula (II)

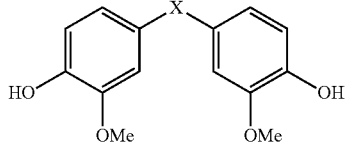
(II)

wherein X is selected from a heteroatom, $C_1$-$C_8$ acyclic, cyclic or heterocyclic linker; and
b) polymerising the monomer to form an oligomer of Formula (I);
wherein the polymerising step comprises forming a C—C bond on the hydroxyphenyl ring of Formula (II).

In some embodiments, the C—C bond is formed at an ortho position on the hydroxyphenyl ring of Formula (II). In this regard, the C—C bond is formed at a 6' position of the hydroxyphenyl ring of Formula (II):

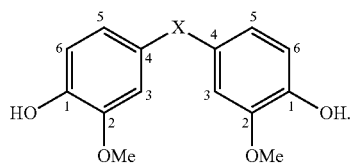
(II)

In some embodiments, the crosslinking or polymerising step is catalysed by an enzyme.

In other embodiments, the crosslinking or polymerising step is catalysed by laccase.

In other embodiments, the polymerising step is performed in a solvent mixture, the solvent mixture comprising an aqueous solvent and another solvent, the combination of which results in a final single phase.

In other embodiments, the monomer of Formula (II) is selected from:

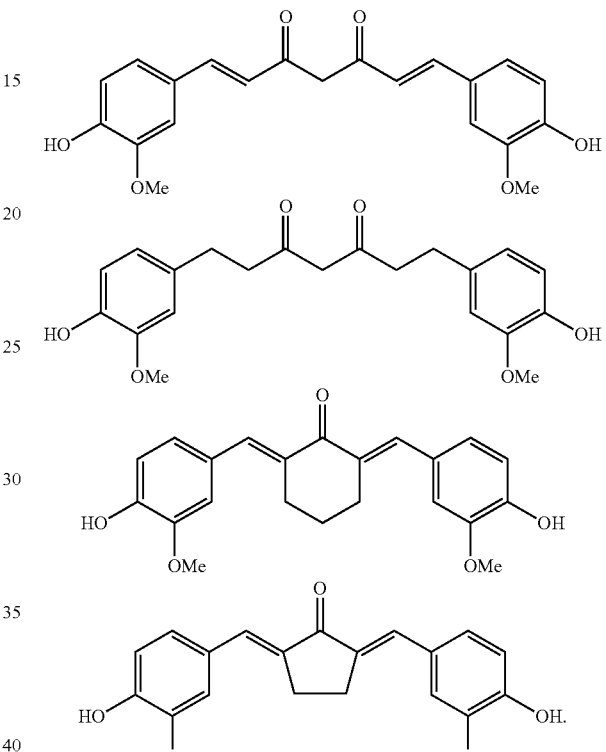

The present invention also discloses a composite, comprising:
a) an oligomer of Formula (I)

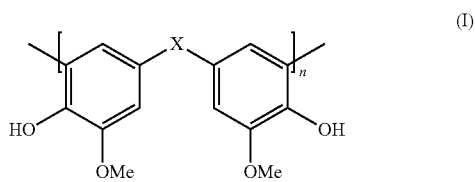
(I)

wherein X is selected from a heteroatom, $C_1$-$C_8$ acyclic, cyclic or heterocyclic linker; and
n is an integer selected from 2 to 15; and
b) a polymer matrix.

In some embodiments, the polymer matrix is selected from polyvinyl chloride (PVC) or polystyrene (PS).

In other embodiments, the oligomer of Formula (I) is present from about 1 wt/wt % to about 10 wt/wt %.

In other embodiments, the composite has a transmittance of more than 90% at about 400 nm to about 800 nm.

In other embodiments, the composite has a degradation of less than 20% after exposure to UV light for 120 h.

In other embodiments, the composite has a leaching rate in 95% ethanol of less than 20%.

BRIEF DESCRIPTION OF DRAWINGS

Some embodiments of the present invention are herein described by way of non-limiting example only, with reference to the accompanying drawings in which.

DETAILED DESCRIPTION

Figure 1:
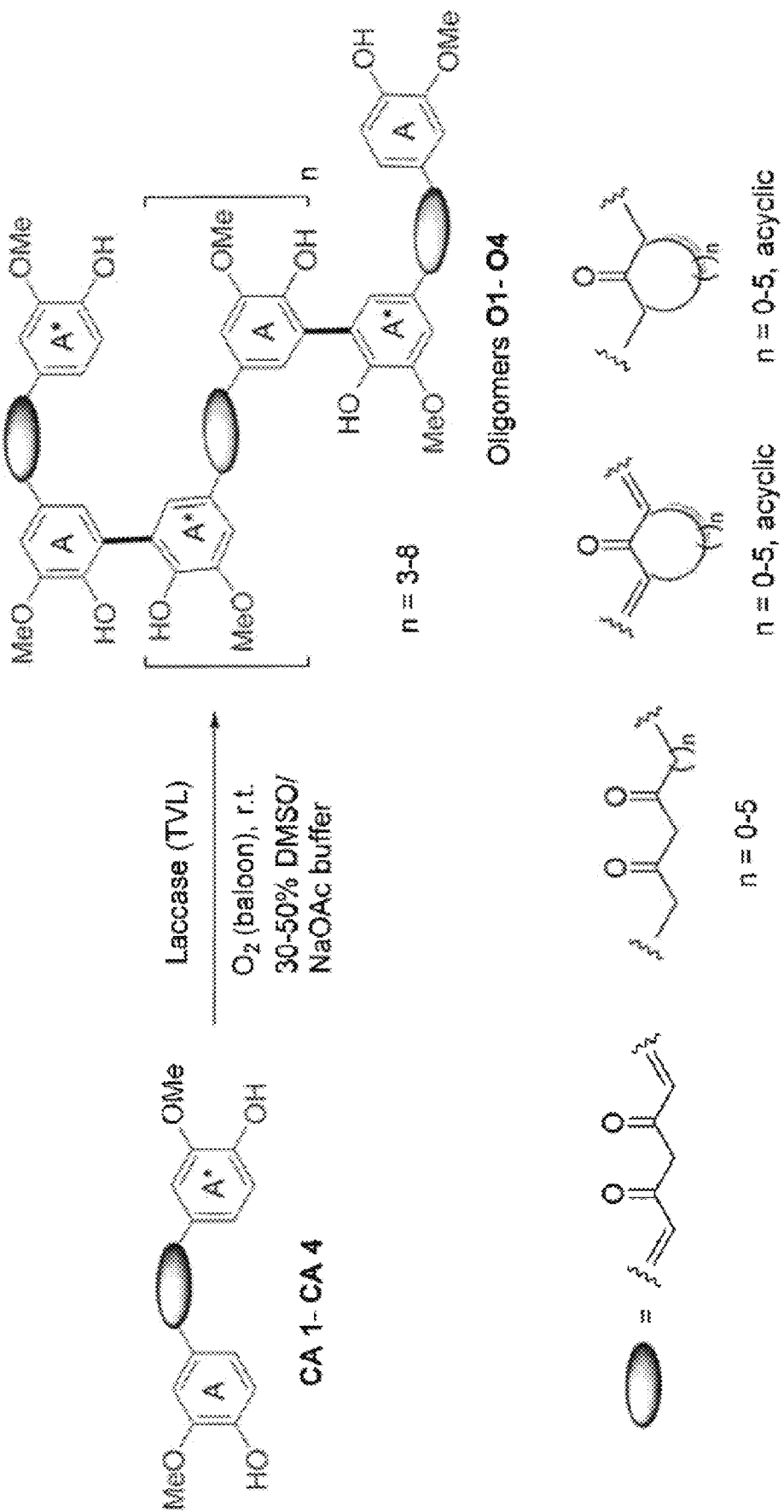
FIG. 1 shows a schematic for the synthesis of oligomers and the exemplary linkages.

The invention describes the synthesis of a series of bio-derived oligomeric materials for use as UV stabilizers for protecting polymers from UV components of sun or artificial light. The oligomers were obtained by laccase-catalysed oxidative polymerization from natural monomers such as curcumin and monomers that are derived from natural vanillin. These bio-derived oligomers have a number average molecular weight in the 1100-2800 Da range, which is appropriate for facile blending into commercial polymers. To evaluate the suitability of the oligomers towards application in food packaging polymers, the bio-derived materials were blended with commonly used food packaging polymers such as polyvinyl chloride (PVC) and polystyrene (PS). As an example, the oligomers were found to protect PS from degradation as good as 2,4-dihydroxybenzophenone, one of the frequently used UV stabilizers in polymer and plastic industries. It was also established that the oligomers show minimum leaching from the formulated polymers under various food simulants tested. The bio-derived oligomers can also be used in applications such as sunscreen protection, textiles, paints and coating industries.

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Acylene" refers to divalent acyl groups —C(O)—.

'Acyclic' refers to a group which contains no rings of atoms, i.e. open chain structure. Aliphatic alkanes are examples of acyclic moieties.

'Cyclic' refers to a group which contains one or more rings of atoms. Aryl, heteroaryl, cycloalkyl groups are examples of cyclic groups.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Heteroaryl" refers to a monovalent aromatic heterocyclic group which fulfils the Huckel criteria for aromaticity (ie. contains 4n+2π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl). It will be understood that where, for instance, R$_2$ or R' is an optionally substituted heteroaryl which has one or more ring heteroatoms, the heteroaryl group can be connected to the core molecule of the compounds of the present invention, through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, R$_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6, 7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Linker" refers to a divalent group which connects (covalent or ionic) one moiety to another moiety. As used herein, the linker covalently connects the two hydroxyphenyl groups to each other via the linker. An acyclic linker refers to a divalent acyclic group, the acyclic group preferably of $C_1$-$C_8$. A cyclic linker refers to a divalent cyclic group (for example aryl, heteroaryl, cycloalkyl) and a heterocyclic linker refers to a divalent heterocyclyl group.

As used herein, 'laccase' is a copper-containing oxidase enzyme found in plants, fungi, and microorganisms. Laccase acts on phenols and similar substrates, performing one-electron oxidations, leading to crosslinking. For example laccases play a role in the formation of lignin by promoting the oxidative coupling of monolignols, a family of naturally occurring phenols.

In the present invention, the advantages are as follows:

(i) The high molecular weight oligomeric materials were synthesized from natural/bio-derived monomers adopting an enzymatic polymerization approach. The UV stabilizers are oligomeric in nature with number average molecular weight in 1100-2800 Da range. This helps the dispersion of the oligomers in a polymer matrix such that a good clarity or transparency can be obtained.

(ii) The monomers are either natural or derived from natural feedstock. These monomers have been shown to be non-toxic.

(iii) The oligomeric materials are bio-derived. In this regard, the oligomers of the present invention are expected to be non-toxic. The materials show similar UV blocking performance like commercial UV stabilizers. The UV blocking ability of the bio-derived oligomers was evaluated after blending with polymers and was found to be as good as the current SOC UV stabilizers. The potential possibility of using bio-derived oligomers as UV blocking materials was verified.

(iv) The oligomers can be synthesized by greener polymerization approach and the monomers are derived from natural feedstocks. For example, oligomers can be synthesized by enzymatic oxidative polymerization. No initiators and metals were used in the synthesis and the process is totally green. The oligomers were already formulated with polymers such as PVC (polyvinyl chloride) and PS (polystyrene) and tested the UV blocking ability. Leaching studies indicated significantly low or no leaching from the formulated polymers in various food simulants—towards application in food packaging polymers.

(v) No radical initiators or heavy metals were used in the synthetic protocol adopted in obtaining the present bio-derived oligomers. The process employs laccase enzyme and air/oxygen were respectively used as a catalyst and an oxidant. Further, as no metal was used as catalyst, there is no concern of metal impurity in the formulated polymers.

(vi) The bio-derived oligomers are neither high molecular weight polymers nor small organic compounds. In contrast to polymeric UV stabilizers, the appropriate molecular weight of the oligomers minimizes the blending issues with other application polymers. Unlike small organic compounds (SOCs), the present oligomers are less prone to leaching from embedded polymers and skin penetration from the formulated skin care products.

Accordingly, the present invention discloses an oligomer of Formula (I):

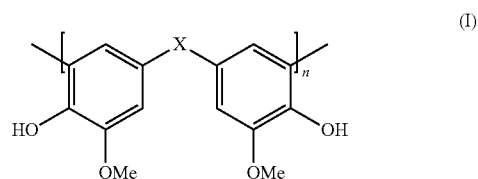

wherein X is selected from a heteroatom, $C_1$-$C_8$ acyclic, cyclic or heterocyclic linker; and n is an integer selected from 2 to 15.

In some embodiments, X is selected from —NH—, —O— or —S—. In other embodiments, X is a $C_4$-$C_8$ acyclic, cyclic or heterocyclic linker. In other embodiments, X is a $C_4$-$C_8$ acyclic, cyclic or heterocyclic linker, the linker comprising at least an acylene moiety. In other embodiments, the linker comprising at least an alkenylene moiety. In other embodiments, the linker comprising at least an alkenylene moiety and at least an acylene moiety. In other embodiments, the linker is j-conjugated.

In some embodiment, X is selected from

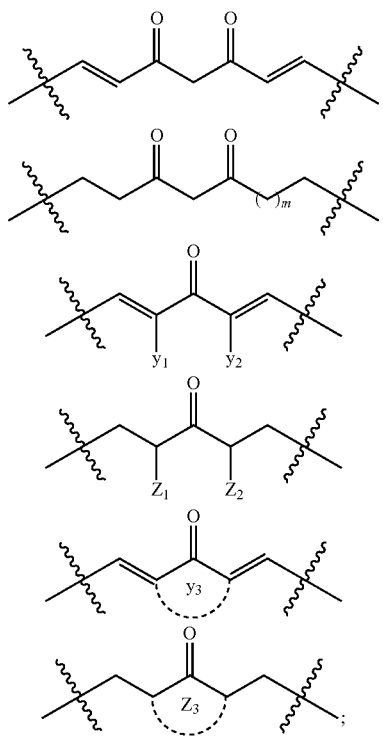

wherein m is an integer selected from 0 to 5;
$Y_1$, $Y_2$, $Z_1$ and $Z_2$ are independently $C_0$-$C_5$ alkyl; and
$Y_3$ and $Z_3$ are independently $C_4$-$C_6$ cycloalkyl.

In other embodiments, m is an integer selected from 0 to 3. In other embodiments, $Y_1$, $Y_2$, $Z_1$ and $Z_2$ are independently selected from H, methyl, ethyl, iso-propyl, n-propyl, n-butyl, iso-butyl, tert-butyl, n-pentyl, iso-pentyl, tert-pentyl, sec-pentyl, neo-pentyl, 3-pentyl, sec-isopentyl or 2-methylbutyl. In other embodiments, $Y_1$, $Y_2$, $Z_1$ and $Z_2$ are independently selected from H, methyl, ethyl, iso-propyl or n-propyl. In other embodiments, X is selected from:

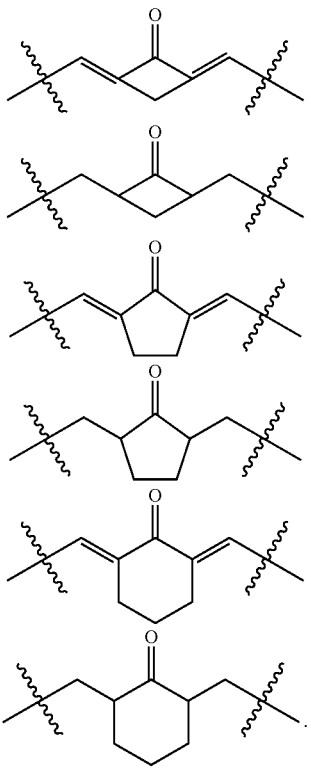

In some embodiments, X is selected from

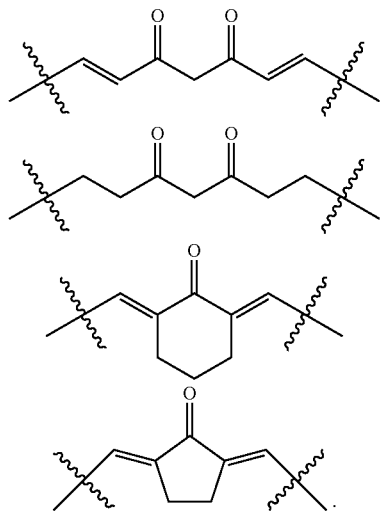

In some embodiments, n is an integer selected from 2 to 15. In other embodiments, n is selected from 2 to 10. In other embodiments, n is selected from 3 to 8. In other embodiments, n is selected from 3 to 7.

In some embodiments, oligomer of Formula (I) has an average molecular weight of about 1000 Da to about 3000 Da. In other embodiments, the average molecular weight of about 1100 Da to about 2900 Da, about 1100 Da to about 2800 Da, about 1100 Da to about 2600 Da, about 1100 Da to about 2500 Da, about 1100 Da to about 2400 Da, about 1100 Da to about 2200 Da, or about 1100 Da to about 2000 Da. In other embodiments, the average molecular weight is about 1000 Da, about 1100 Da, about 1200 Da, about 1400 Da, about 1600 Da, about 1800 Da, about 2000 Da, about 2200 Da, about 2400 Da, about 2600 Da, about 2700 Da, about 2800 Da, about 2900 Da or about 3000 Da.

In some embodiments, the oligomer of Formula (I) has a polydispersity index (Mw/Mn) of about 1.0 to about 1.3. In other embodiments, the polydispersity index is about 1.1 to about 1.2.

In some embodiments, the oligomer of Formula (I) has a UV absorption within the range of about 200 nm to about 500 nm. In other embodiments, the range is about 250 nm to about 450 nm, or about 300 nm to about 450 nm. In other embodiments, the UV absorption is at about 200 nm, about 220 nm, about 240 nm, about 260 nm, about 280 nm, about 300 nm, about 350 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm or about 500 nm.

In some embodiments, the oligomer of Formula (I) has a molar extinction coefficient of more than 30,000 $M^{-1}$ $cm^{-1}$. The molar extinction coefficient (E) is a measure of how strongly a chemical species absorbs light at a particular wavelength. It is an intrinsic property of chemical species that is dependent upon their chemical composition and structure. The molar extinction coefficient can be determined at each oligomer's respective wavelength of maximum absorption ($\lambda_{max}$). In other embodiments, the molar extinction coefficient is more than 31,000 $M^{-1}$ $cm^{-1}$, more than 32,000 $M^{-1}$ $cm^{-1}$, more than 35,000 $M^{-1}$ $cm^{-1}$, more than 40,000 $M^{-1}$ $cm^{-1}$, more than 45,000 $M^{-1}$ $cm^{-1}$ or more than 50,000 $M^{-1}$ $cm^{-1}$.

The present invention also discloses a method of forming an oligomer, the method including the step of:
a) providing a monomer of Formula (II)

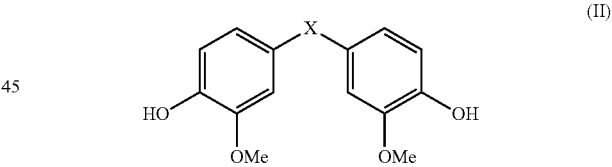

(II)

wherein X is selected from a heteroatom, $C_1$-$C_8$ acyclic, cyclic or heterocyclic linker; and
b) polymerising the monomer to form an oligomer of Formula (I);
wherein the polymerising step comprises forming a C—C bond on the hydroxyphenyl ring of Formula (II).

In some embodiments, the monomer of Formula (II) is selected from

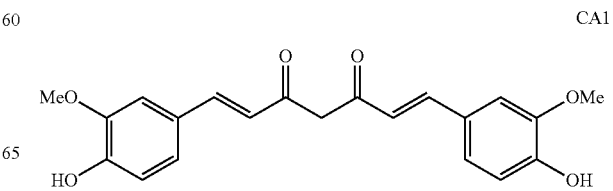

CA1

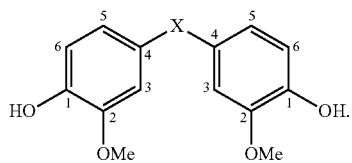

(II)

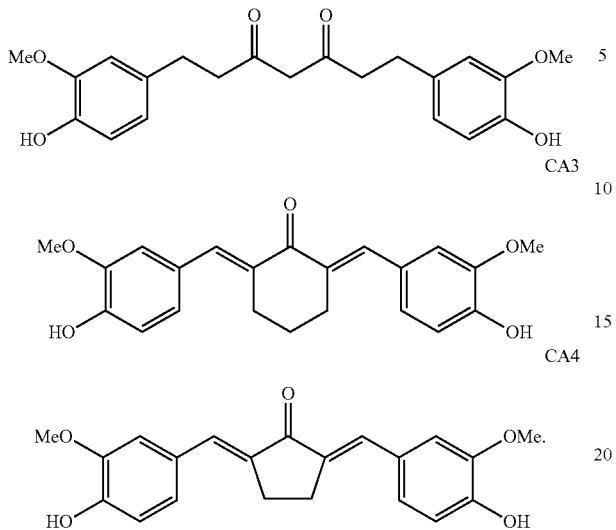

Accordingly, the oligomers that can be synthesised from these monomers are as follows:

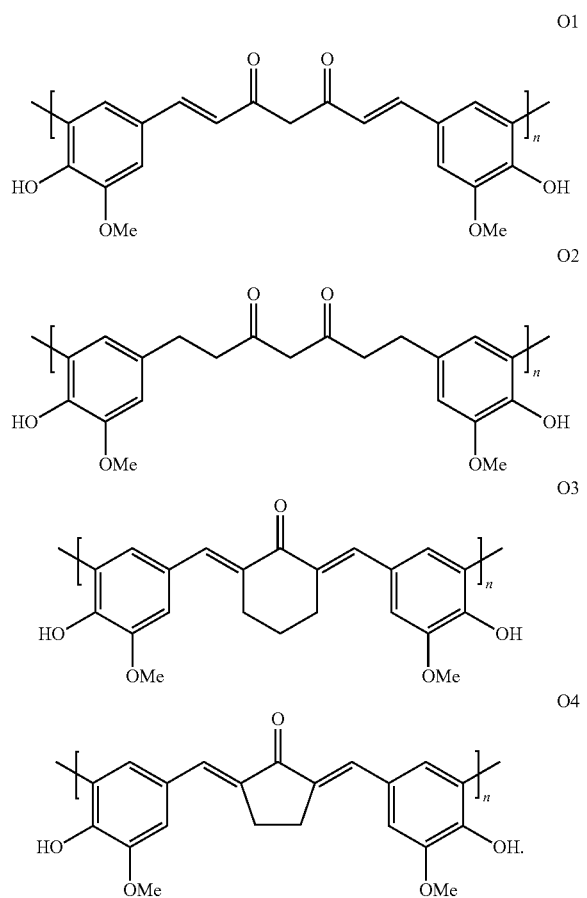

In some embodiments, the C—C bond is formed at an ortho position on the hydroxyphenyl ring of Formula (II). In this regard, the C—C bond is formed at a 6' position of the hydroxyphenyl ring of Formula (II):

A carbon-carbon (C—C) bond is a covalent bond between two carbon atoms. In this regard, it is a single bond: a bond composed of two electrons, one from each of the two atoms. The carbon-carbon single bond is a sigma bond and is formed between one hybridized orbital from each of the carbon atoms. Advantageously, the C—C bond has a bond energy of about 346 kJ/mol and is less prone to hydrolysis. This makes the oligomer less prone to degradation and accordingly, can also improve its stability when used as a UV stabiliser.

When at least two C—C bonds are formed between 3 compounds of Formula (II), an oligomer of Formula (I) is obtained. In some embodiments, oligomer of Formula (I) comprises 3 to 15 monomers. In other embodiments, oligomer of Formula (I) comprises 3 to 12 monomers, 4 to 10 monomers or 5 to 10 monomers. In other embodiments, oligomer of Formula (I) comprises at least 3 monomers, at least 4 monomers, at least 5 monomers, at least 6 monomers, at least 7 monomers, at least 8 monomers, at least 9 monomers, at least 10 monomers, at least 11 monomers, at least 12 monomers, at least 13 monomers, at least 14 monomers or at least 15 monomers.

In some embodiments, the crosslinking or polymerising step is catalysed by an enzyme. In other embodiments, the crosslinking or polymerising step is catalysed by laccase. In other embodiments, the crosslinking or polymerising step is catalysed by peroxidases.

In some embodiments, the polymerising step is performed for at least 2 h. In other embodiments, the polymerising step is performed for at least 3 h, at least 4 h, at least 5 h, at least 8 h, at least 12 h or at least 24 h.

In some embodiments, the polymerising step is performed at ambient temperature. In other embodiments, the polymerising step is performed at about 15° C., about 20° C., about 25° C., about 30° C., about 35° C., about 40° C. or about 45° C.

In some embodiments, the polymerising step is performed in a solvent mixture. As used herein, the solvent mixture refers to a mixture of an aqueous solvent and another solvent, the combination of which results in a final single phase. The aqueous solvent can include dissolved ions, salts and molecules such as amino acids, proteins, sugars and phospholipids.

Such salts may be, but not limited to, sodium chloride, potassium chloride, ammonium acetate, magnesium acetate, magnesium chloride, magnesium sulfate, potassium acetate, potassium chloride, sodium acetate, sodium citrate, zinc chloride, HEPES sodium, calcium chloride, ferric nitrate, sodium bicarbonate, potassium phosphate and sodium phosphate. As such, biological fluids, physiological solutions and culture medium also falls within this definition. The another solvent can be either polar or non-polar, and/or either protic or aprotic. Another solvent can include, and is not limited to, pentane, cyclopentane, hexane, cyclohexane, benzene, toluene, dioxane, chloroform, diethylether, dichloromethane, tetrahydrofuran, ethyl acetate, acetone, dimethylformamide, acetonitrile, dimethyl sulfoxide, nitromethane, propylene carbonate, formic acid, butanol, isopropanol, propanol, ethanol, methanol, acetic acid, ethylene glycol, diethylene glycol, water or a combination thereof.

In some embodiments, the solvent mixture comprises dimethylformamide (DMF) and water.

In other embodiments, the solvent mixture comprises acetone and water.

In some embodiments, the method of forming an oligomer includes the steps of:
a) providing a monomer of Formula (II)

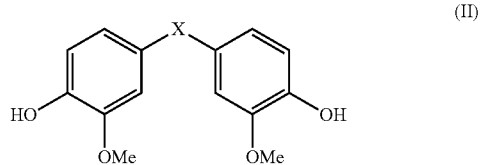

(II)

wherein X is selected from a heteroatom, $C_1$-$C_8$ acyclic, cyclic or heterocyclic linker; and
b) polymerising the monomer to form an oligomer of Formula (I);
wherein the polymerising step comprises forming a C—C bond on the ortho position on the hydroxyphenyl ring of Formula (II).

In some embodiments, the method of forming an oligomer includes the steps of:
a) providing a monomer of Formula (II)

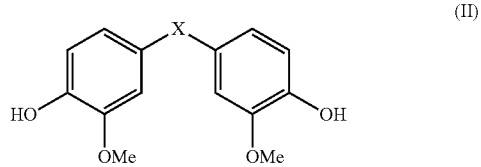

(II)

wherein X is selected from a heteroatom, $C_1$-$C_8$ acyclic, cyclic or heterocyclic linker; and
b) polymerising the monomer to form an oligomer of Formula (I);
wherein the polymerising step comprises forming a C—C bond on the ortho position on the hydroxyphenyl ring of Formula (II); and
wherein the polymerising step is catalysed by laccase.

The present invention also discloses a composite, comprising:
a) an oligomer of Formula (I) as disclosed herein; and
b) a polymer matrix.

As used herein, 'polymer matrix' refers to a continuous phase in the composite used to hold a dispersed phase in its place. Polymer matrix is typically classified as thermoset or thermoplastic. Thermoset polymer on curing results three-dimensional cross-linked solid structure having dimensional/thermal stability and solvent-resistant properties. Polyesters, vinyl esters, epoxies, phenolics, and polyamides are examples of thermosets. Thermoplastic polymers can be molded, melted, and remolded without altering its physical properties. Thermoplastic include polyesters, polyamide-imide, polyetherimide, polyether ether ketone (PEEK), polyphenylene sulfide, and liquid crystal polymers.

The oligomer of Formula (I) can be incorporated into the polymer matrix via any known method. For example, solvent casting can be used. In solvent casting, a polymer is dissolved in an organic solvent. Oligomer of Formula (I) can then added to the solution. The mixture is shaped into its final geometry. For example, it can be cast onto a glass plate to produce a membrane or in a three-dimensional mold. When the solvent evaporates, it creates a composite material consisting of oligomer of Formula (I) together with the polymer.

The oligomer of Formula (I) can be incorporated into a polymer matrix for providing the matrix with an UV absorption functionality. In some embodiments, the polymer matrix is polyvinyl chloride (PVC). In other embodiments, the polymer matrix is polystyrene (PS). In other embodiments, the polymer matrix is selected from PVC, PS, polyethylene terephthalate (PET), polypropylene (PP), high density polyethylene (HDPE) or a combination thereof.

The oligomer of Formula (I) can be added to the polymer matrix at various concentrations to provide a composite with varying UV absorption strength. In some embodiments, oligomer of Formula (I) is added from about 1 wt/wt % to about 10 wt/wt %. In other embodiments, oligomer of Formula (I) is added from about 1 wt/wt % to about 9 wt/wt %, about 1 wt/wt % to about 8 wt/wt %, about 1 wt/wt % to about 7 wt/wt %, about 1 wt/wt % to about 6 wt/wt %, about 2 wt/wt % to about 6 wt/wt %, about 3 wt/wt % to about 6 wt/wt % or about 4 wt/wt % to about 6 wt/wt %. In other embodiments, oligomer of Formula (I) is added at about 1 wt/wt %, about 2 wt/wt %, about 3 wt/wt %, about 4 wt/wt %, about 5 wt/wt %, about 6 wt/wt %, about 7 wt/wt %, about 8 wt/wt %, about 9 wt/wt % or about 10 wt/wt %.

The composite is able to block the UV light in a wider spectrum (400-200 nm). In some embodiments, the composite has a transmittance of more than 90% at about 400 nm to about 800 nm. In other embodiments, the transmittance is from about 450 nm to about 800 nm, about 500 nm to about 800 nm. In other embodiments, the transmittance is more than 91%, more than 92%, more than 93%, more than 94%, more than 95%, more than 96%, more than 97%, more than 98% or more than 99%. In other embodiments, the transmittance is 100%.

The presence of the oligomer in the composite is able to retard the degradation of the polymer matrix. In other words, the oligomer protects the polymer from degradation. In some embodiments, composite is degraded less than 20% after exposure to UV light for 120 h. In other embodiments, the degradation is less than 19%, less than 18%, less than 15%, less than 12%, less than 10%, less than 8% or less than 5%.

In some embodiments, the composite has a leaching rate in 95% ethanol of less than 20%. In other embodiments, the leaching rate is less than 19%, less than 18%, less than 17%, less than 16%, less than 15%, less than 14%, less than 13%, less than 12%, less than 11%, less than 10%, less than 9%, less than 8%, less than 7%, less than 6% or less than 5%. In other embodiments, the composite has a leaching rate in water or 3% acetic acid of 0%.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

In order to minimize the use of small organic compounds (SOCs), high molecular weight macromolecular and polymeric UV stabilizers were developed with good performance as is demonstrated herein. The materials were synthesized from synthetic sources by adopting conventional chemical methods.

These materials produced by enzymatic reactions such as oxidative polymerization by oxidases such as laccase and peroxidases is an elegant sustainable approach to produce polymers or oligomers that are difficult to obtain by conventional chemical polymerization methods.

The synthesis of the oligomers can be from natural or bio-derived monomers. Curcumin (CA 1) is produced by the turmeric plant (*Curcuma longa*) and its hydrogenated analogue (CA 2) was obtained by hydrogenation. CA 3 and CA 4 were obtained from simple Aldol condensation of cyclic ketone and vanillin, a commonly used flavouring additive which originates from the vanilla bean.

Figure 2:
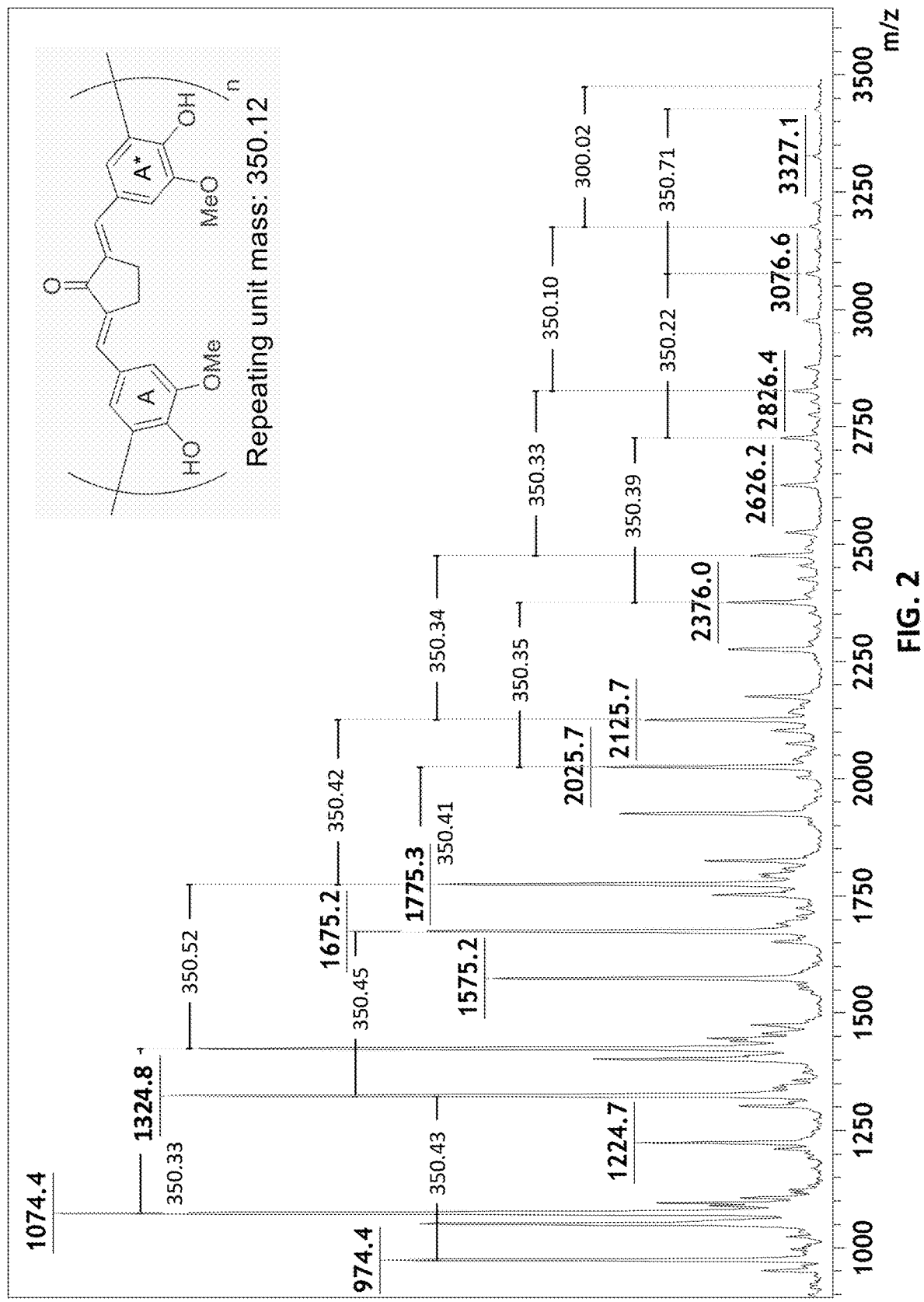
FIG. 2 illustrates a matrix-assisted laser desorption/ionisation time-of-flight mass spectroscopy (MALDI-TOF-MS) analysis result of an exemplary oligomer.

The oligomers were synthesized by laccase-catalysed oxidative polymerization of CA 1-CA 4 (FIG. 1) in aqueous-organic reaction media using oxygen/air as the oxidant. The oligomerization proceeded smoothly and afforded the oligomers O1-O4 in 84-93 wt % yields respectively from CA 1-4. Analysis of the oligomers by high performance liquid chromatography (HPLC) indicated the complete utilization of monomers during the polymerization. The oligomers were found to possess a number average molecular weight in the 1700-2800 Da range and low polydispersity index (Mw/Mn=1.1-1.2) as observed by gel permeation chromatography (GPC) and matrix-assisted laser desorption/ionisation time-of-flight mass spectroscopy (MALDI-TOF-MS) analysis (Table 1). The repeating molecular mass 366.4 Da, 370.2 Da, 364.4 Da and 350.5 Da observed respectively for the oligomers O1-O4 corresponded to the monomer with two hydrogen atoms removed (M-2H) (FIG. 2). Based on the higher molecular mass observed, the oligomers are estimated to contain 5-10 units of the monomers.

TABLE 1

GPC and MALDITOF-MS data for oligomers

| Mono-mers | Oligo-mers | Yield (wt %) | GPC[c] $M_n$ (Da) | $M_w$ (Da) | $M_w/M_n$ | MALDI-TOF-MS[d] $M_n$ (Da) | $M_w$ (Da) | $M_w/M_n$ |
|---|---|---|---|---|---|---|---|---|
| CA 1 | O1 | 84 | n.d.[e] | n.d.[e] | n.d.[e] | 1430 | 1600 | 1.12 |
| CA 2[b] | O2 | 84 | 2030 | 2370 | 1.17 | 1110 | 1200 | 1.08 |
| CA 3 | O3 | 93 | 2600 | 2820 | 1.08 | 1500 | 1710 | 1.14 |
| CA 4 | O4 | 92 | 2880 | 3130 | 1.09 | 1510 | 1730 | 1.14 |

[a] Reaction conditions: 0.05 mmol of CA 1, 3 and 4, 4 mL DMF, in 4 mL sodium acetate buffer; reaction time: 3 h, reaction temp.: 25° C.
[b] Reaction conditions: 0.05 mmol of CA 2, 1.5 mL acetone, in 2.5 mL sodium acetate buffer; reaction time: 3 h, reaction temp.: 25° C.;
[c] PMMA was used for calibration;
[d] DCTB matrix with NaTFA cationic salt;
[e] Not determined due to poor solubility of O1 in conventional solvents used to run GPC.

Figure 3:
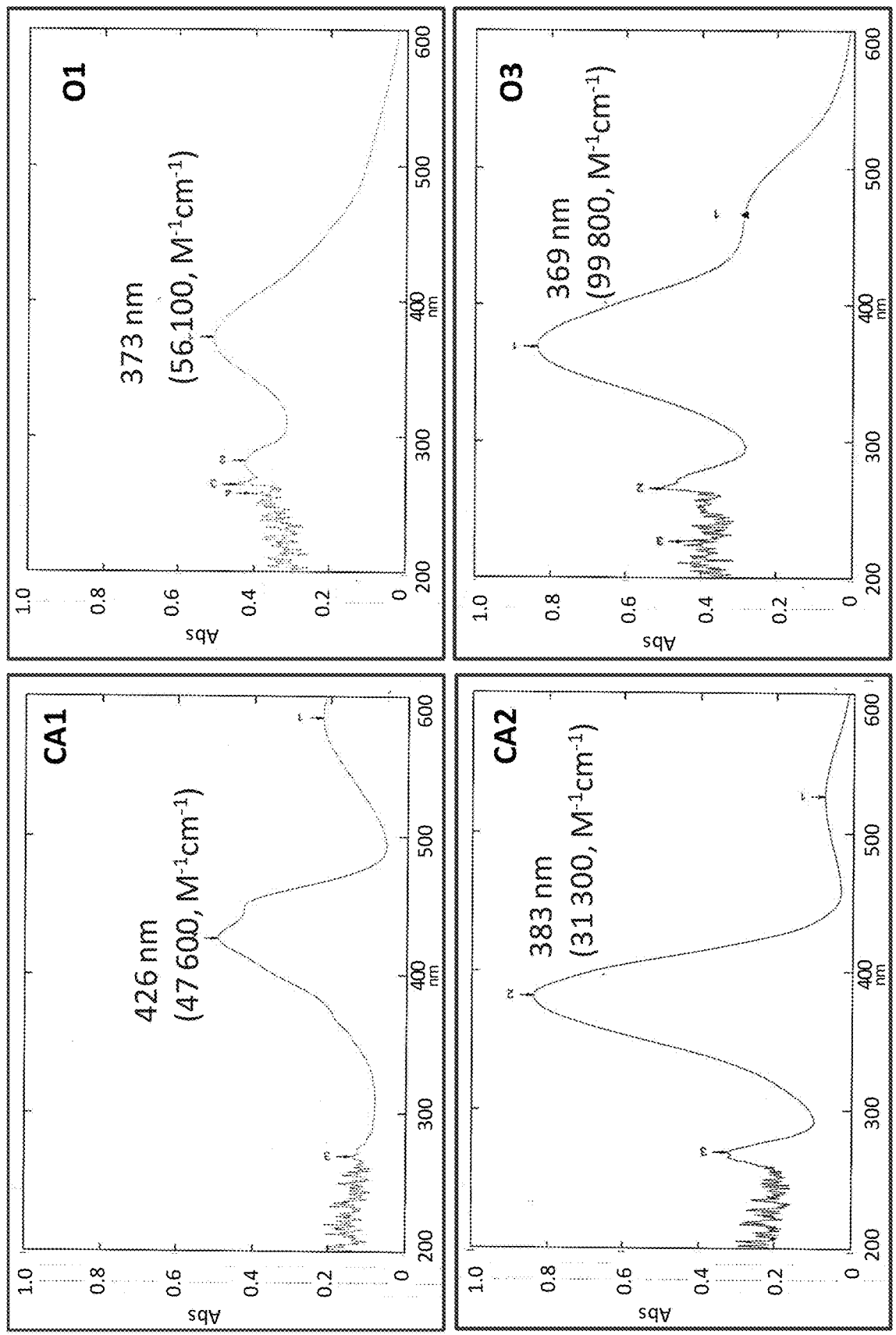
FIG. 3 illustrates representative UV-vis spectra of the monomers and the oligomers.

UV absorption studies: As an initial evaluation, the UV-Vis absorption spectra of oligomers O1-O4 were measured in DMF solutions (representative spectra are shown in FIG. 3). All the oligomers showed an intense band in the UV region with high molar extinction coefficient (Table 2), suggesting that the oligomers are capable of absorbing UV light effectively. The UV-Vis absorption data for 2,4-dihydroxybenzophenone (DHBP), a commercially available synthetic UV stabilizer, is provided for comparison (Table 2).

TABLE 2

UV absorption data for the monomers and oligomers.

| Compounds | $\lambda$ (nm) | $\varepsilon$ (M$^{-1}$cm$^{-1}$) | $\varepsilon$ (L g$^{-1}$cm$^{-1}$) |
|---|---|---|---|
| CA 1 | 585 | 21 410 | 58.1 |
|  | 426 | 47 640 | 129.3 |
| CA 2 | 285 | 13 620 | 36.6 |
| CA 3 | 527 | 2 690 | 7.3 |
|  | 383 | 31 330 | 85.5 |
|  | 270 | 12 190 | 33.3 |
| CA 4 | 550 | 15 760 | 44.7 |
|  | 413 | 33 810 | 95.9 |
|  | 273 | 10 820 | 30.7 |
| O1[a] | 373 | 56 100 | 39.0 |
|  | 282 | 46 800 | 32.5 |
| O2[a] | 289 | 32 150 | 28.9 |
| O3[a] | 467 | 34 300 | 22.9 |
|  | 369 | 99 790 | 66.5 |
|  | 266 | 59 880 | 39.9 |
| O4[a] | 492 | 35 780 | 23.6 |
|  | 395 | 91 950 | 60.7 |
|  | 272 | 46 900 | 30.9 |
| DHBP | 325 | 10 000 | 46.7 |
|  | 292 | 12 900 | 60.3 |

[a] Mn values from MALDI-TOF-MS have been used to calculate the concentration.

Figure 4:
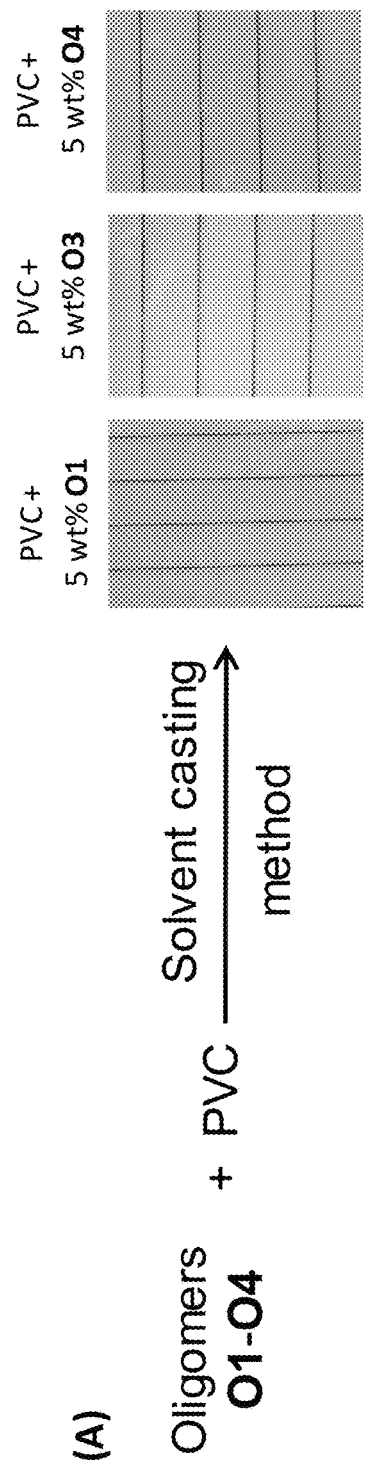
FIG. 4 illustrates (A) the incorporation of oligomers into polymer matrix (PVC) by solvent casting method and representative oligomer-embedded PVC films and (B) transmittance spectra of oligomer-embedded films.
Figure 4:
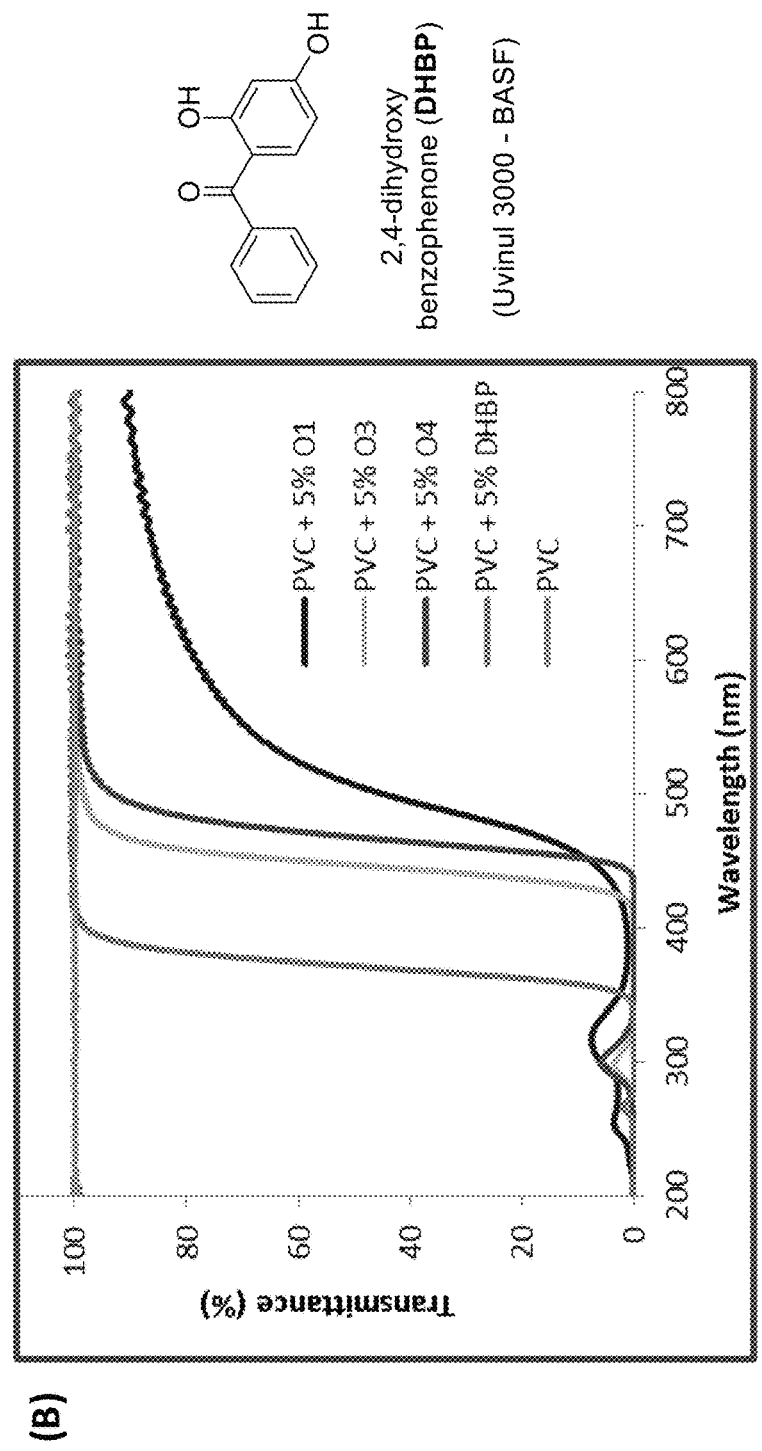

Transmittance and UV blocking characteristics of embedded films: The oligomers O1-O4 (5 wt %) were blended with polyvinyl chloride (PVC) and polystyrene (PS), which are widely used for food packaging applications. For uniform distribution of the oligomers in the polymers, the solvent casting method was adopted and the oligomer-embedded films were prepared using a film applicator. All the films exhibited similar UV absorption characteristics as that of the oligomers in the solution. The UV-Vis transmittance spectra of the oligomers O1-O4 embedded PVC films are provided in FIG. 4B; all the oligomers were found to block UV A (320-400 nm) and UV 8 (280-320 nm) and some components of UVC (100-280 nm) completely. The UV-Vis transmittance spectrum of a blank PVC film (without any UV blockers) showed that all UV and visible light passed through the film (FIG. 4B). The transmittance behaviour of a well-known synthetic UV stabilizer (DHBP) is provided for comparison. The above observations indicated that bio-derived oligomers could potentially be used as UV blockers for the entire UV region.

Figure 5:
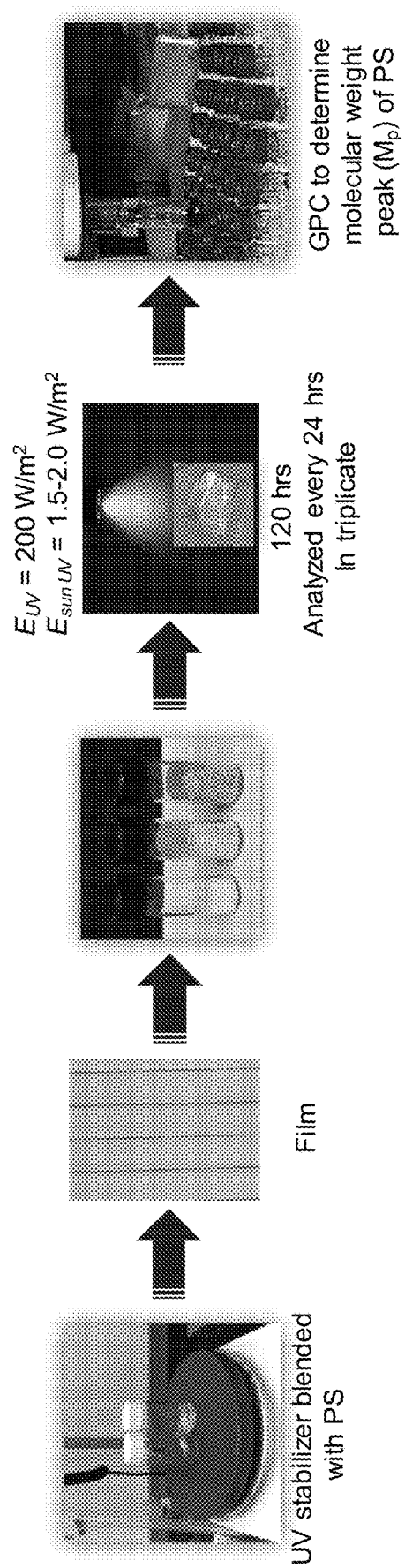
FIG. 5 illustrates the protocol for the incorporation oligomers into polymer matrix (PS) by solvent casting method and subsequent exposure of oligomer-embedded PS films to UV light.
Figure 6:
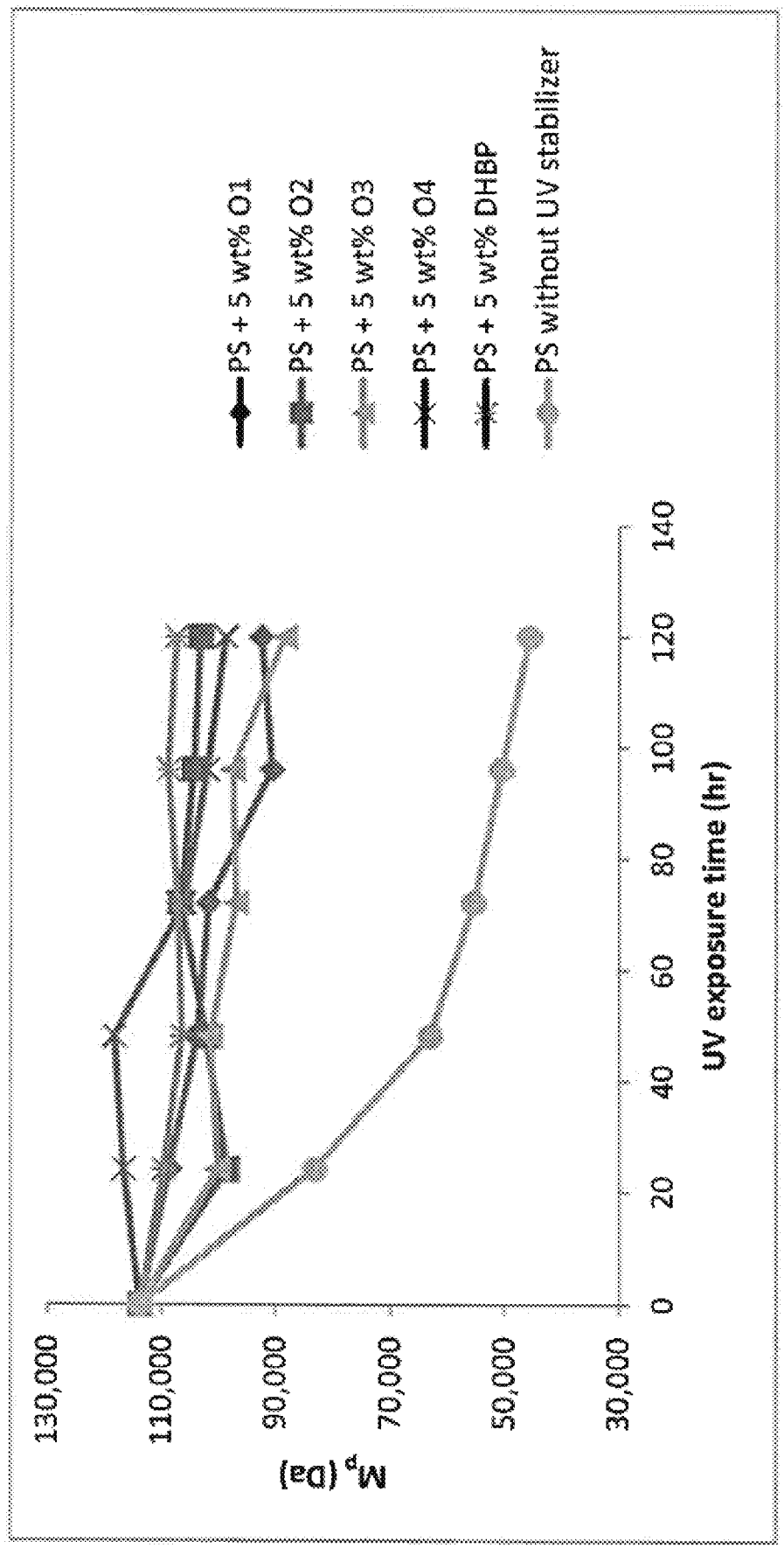
FIG. 6 illustrates the observed $M_p$ (molecular weight of the highest peak) values from GPC before (0 h) and after UV exposure. The averaged $M_p$ values from three different experiments were taken.

UV blocking ability of oligomers in protecting polystyrene: To determine the UV protection ability of the oligomers, the materials were blended with PS by the solvent casting method (FIG. 5). The oligomer blended PS was exposed to UV irradiation (200 W/m², >150 times stronger than the Sun's UV irradiance) for 120 hours. After 24 h, three samples (6-7 mg each) were taken out from each batch for GPC analysis. The averaged Mp values from GPC were used in the plot (FIG. 6). Polystyrene without UV stabilizer showed a steady and significant decrease in Mp with increasing UV exposure time. In contrast, O1-O4 embedded PS showed relatively minimum decrease in Mp over 120 hours of UV exposure. This is equivalent to 110 days of outdoor testing (based on Q Lab's protocol; 280 000 KJ=Irradiance (W/m²)×Hours×3.6, which is equivalent to 1 year total UV irradiance in Florida). In fact, their light protection ability is comparable to that of the commercial UV absorber DHBP. The above study clearly indicates that oligomers O1-O4 could potentially be used as UV stabilizers for various applications.

Leaching studies: FDA recommended food simulants
  pure water
  15% EtOH in water (mimics alcohol-containing foods)
  3% acetic acid in water (mimics acid-containing foods)
  95% EtOH in water (heptane substitute for PS, mimics fat-containing food)

Figure 7:
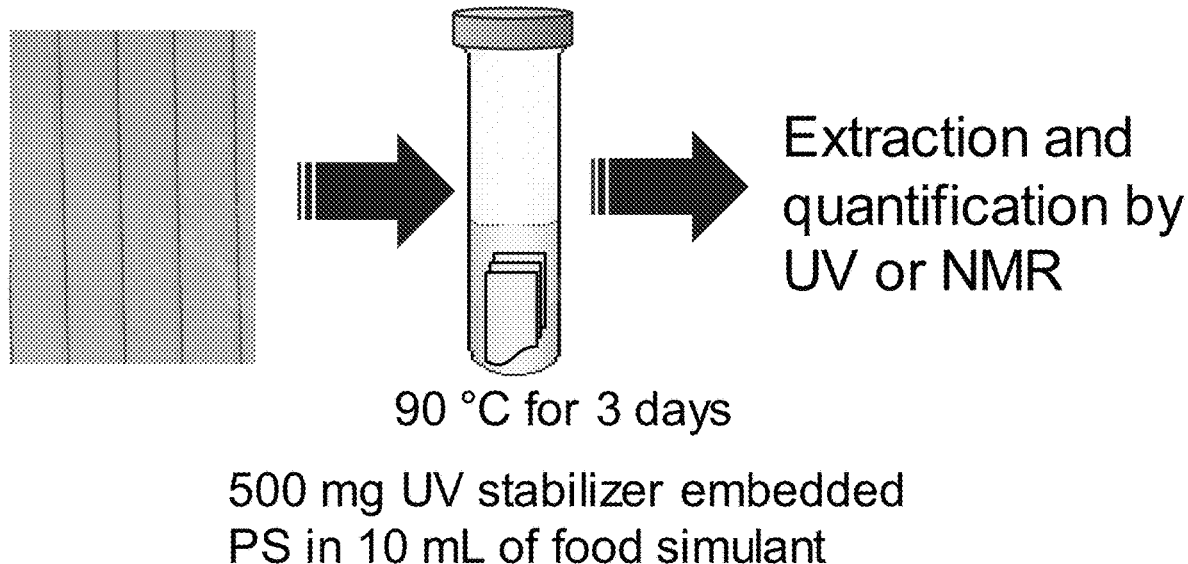
FIG. 7 illustrates the protocol for leaching experiments and the comparator compounds used.
Figure 7:
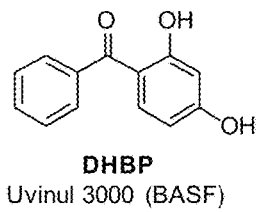
Figure 7:
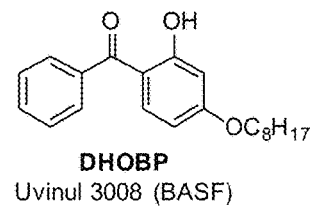
Figure 7:
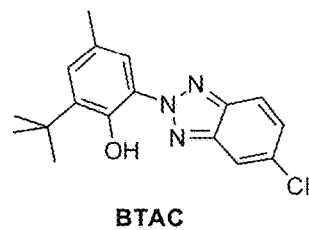
Figure 7:
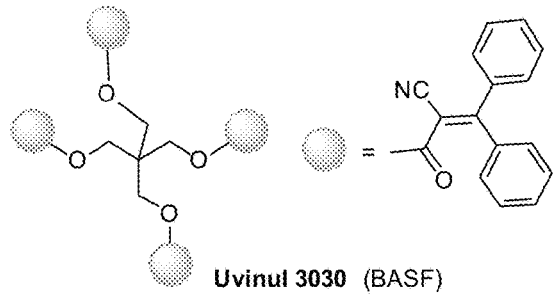
Figure 8:
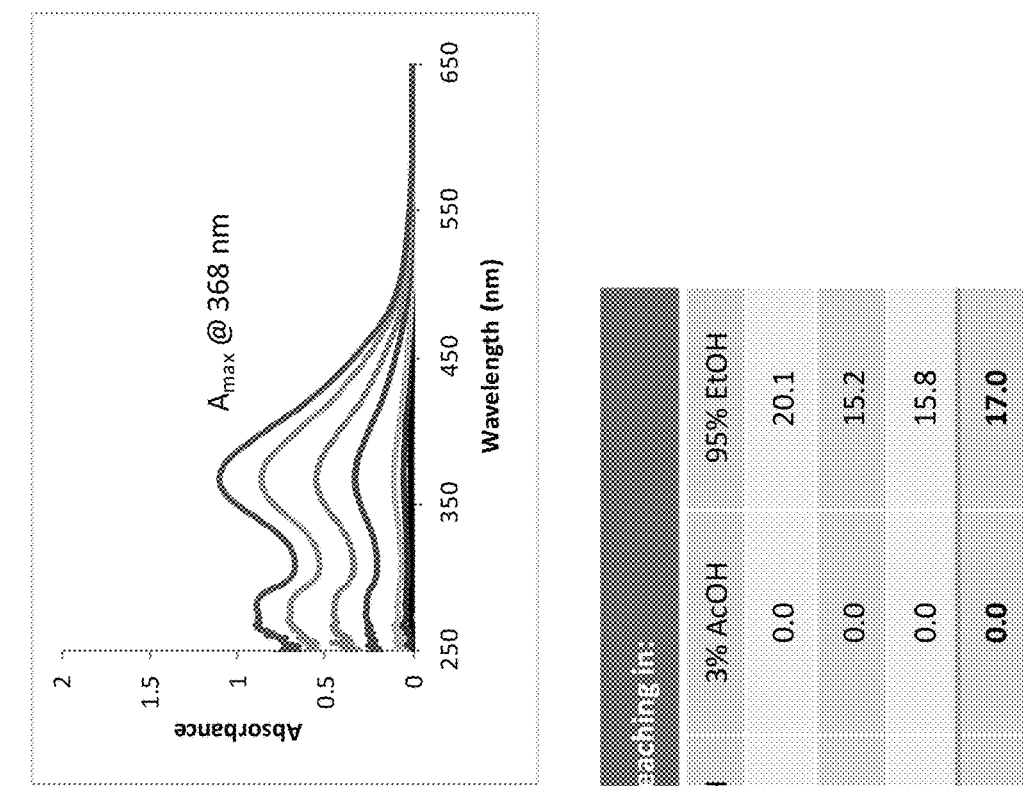
FIG. 8 illustrates results of leaching studies for 01.
Figure 8:
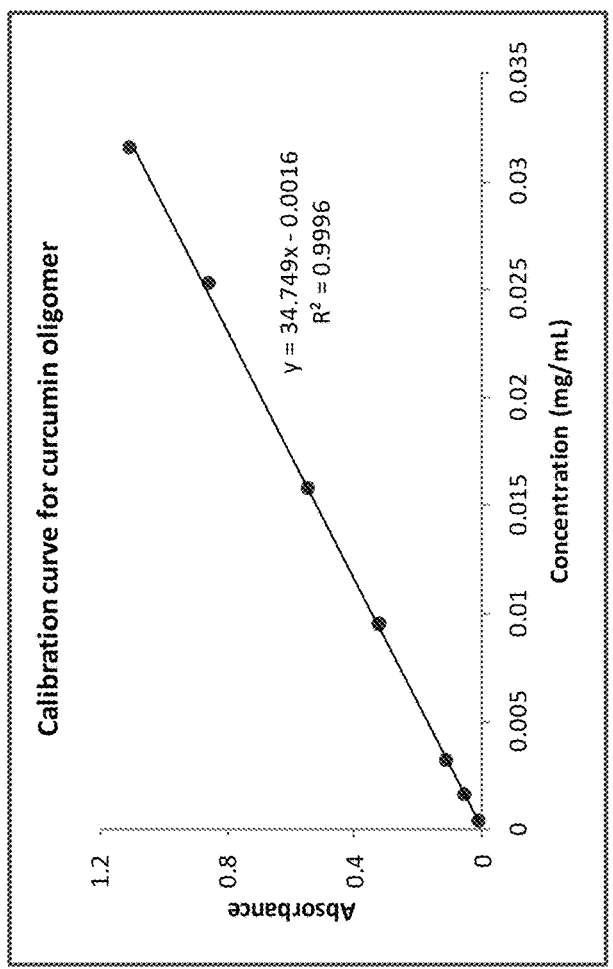
Figure 9:
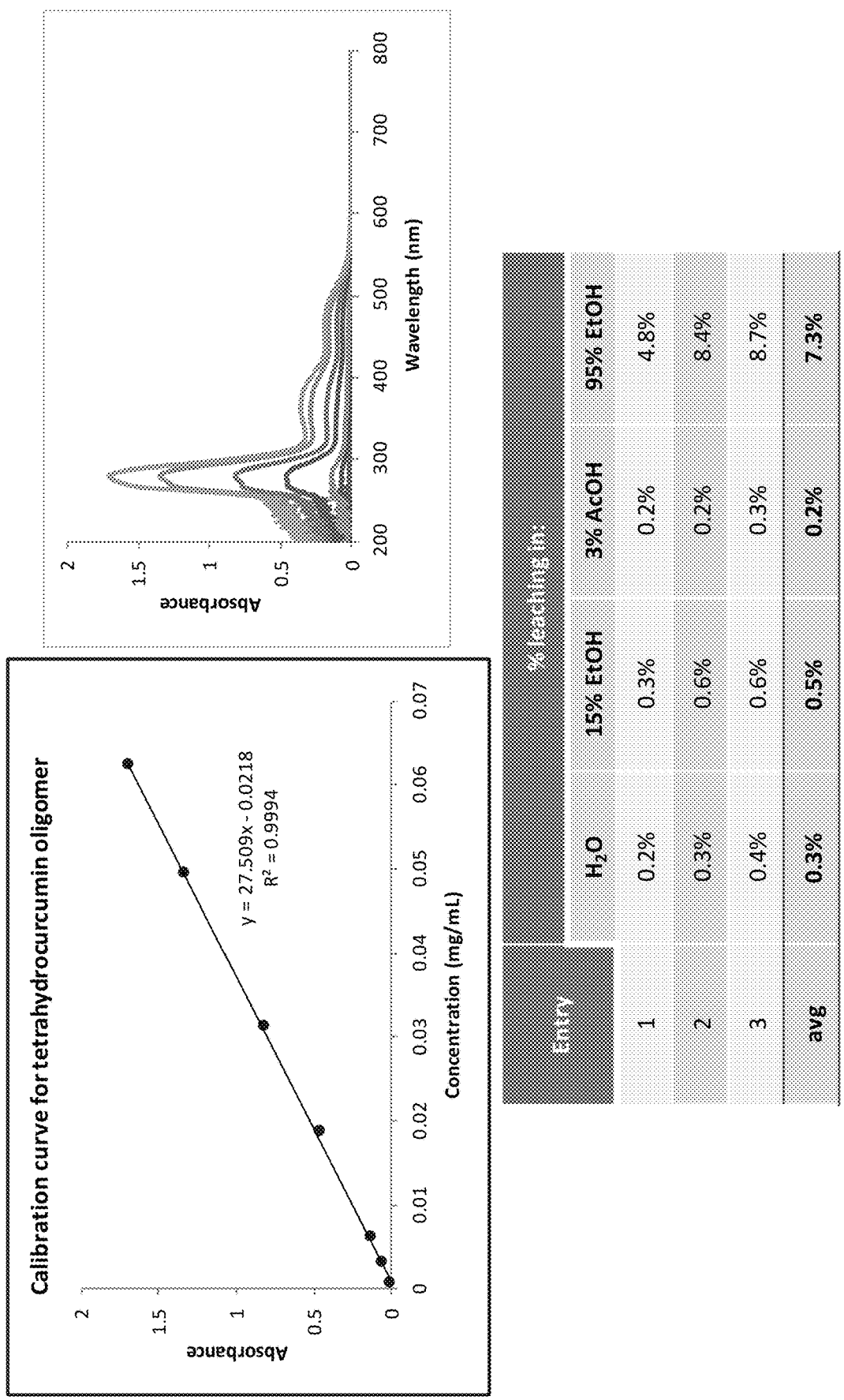
FIG. 9 illustrates results of leaching studies for 02.
Figure 10:
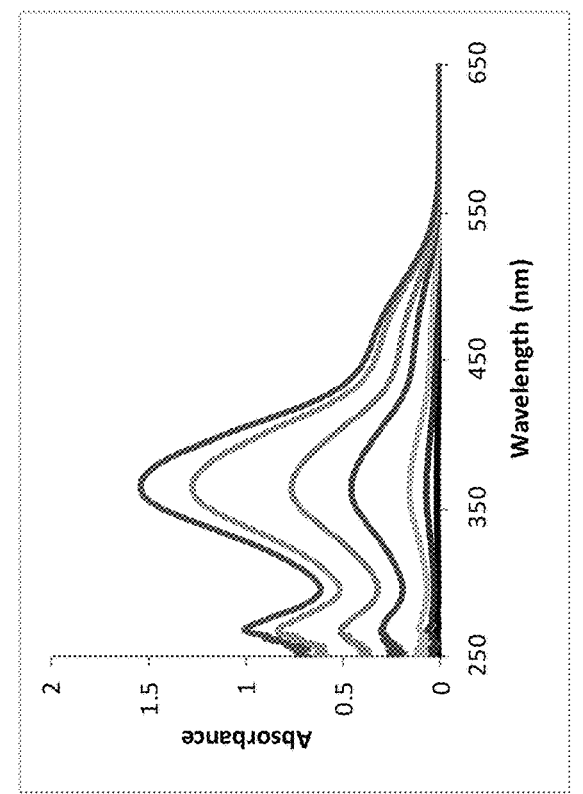
FIG. 10 illustrates results of leaching studies for 03.
Figure 10:
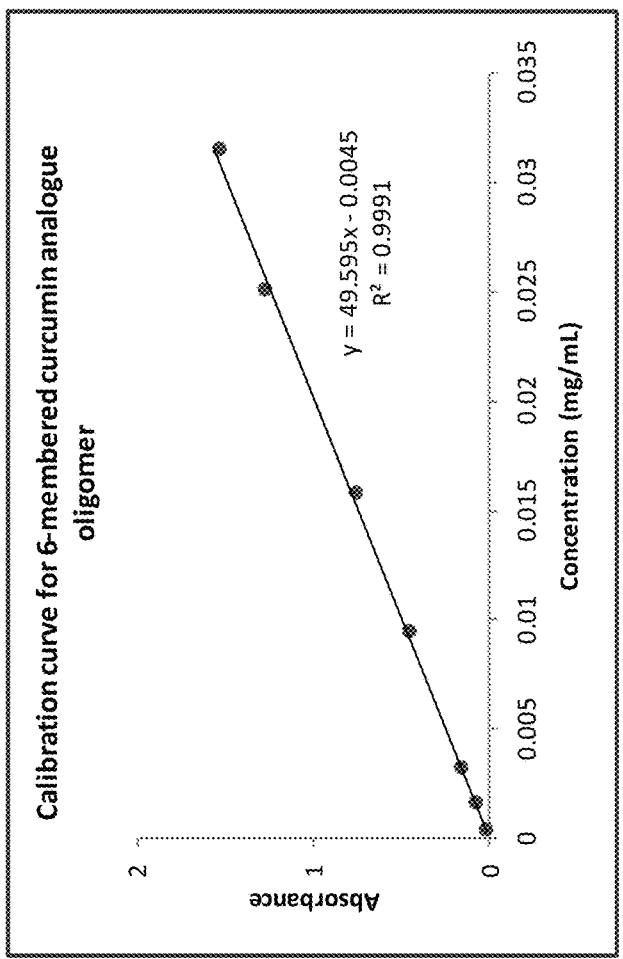
Figure 11:
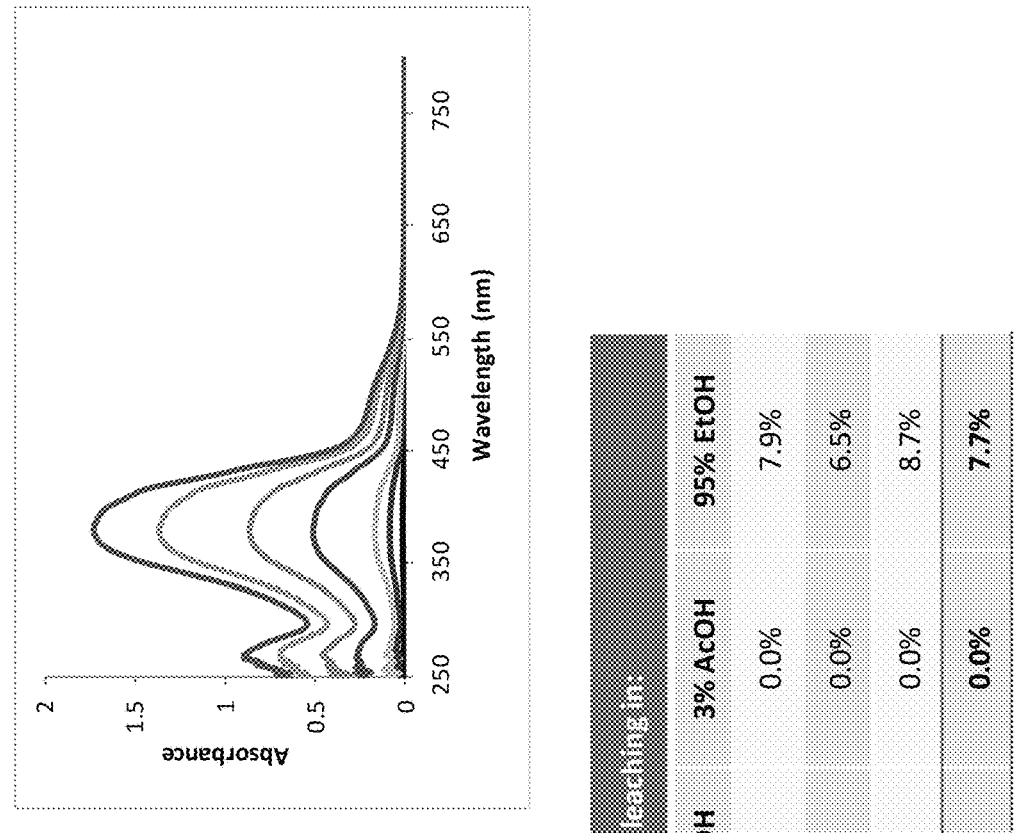
FIG. 11 illustrates results of leaching studies for 04.
Figure 11:
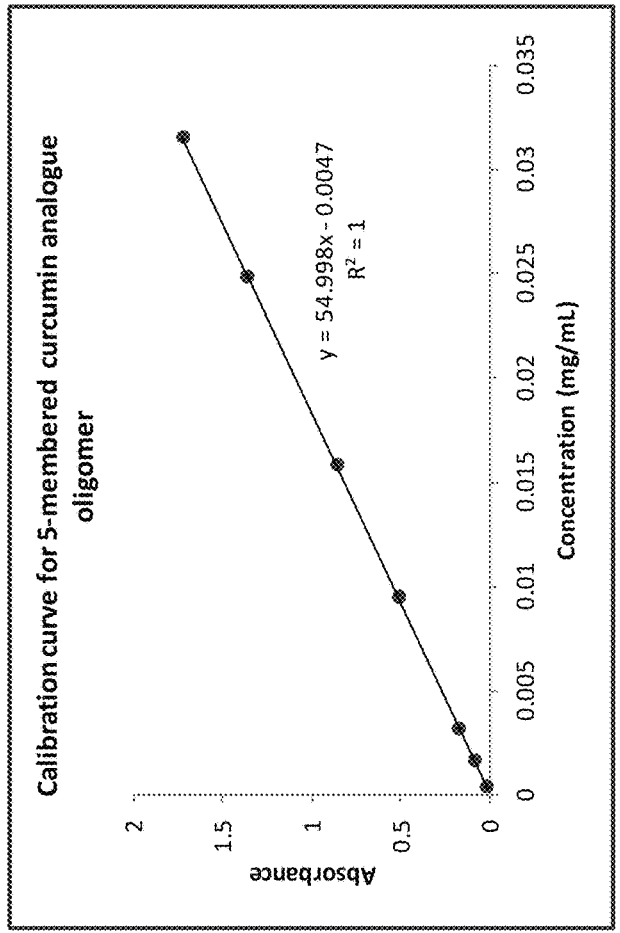

The protocol is presented in FIG. 7. The results of the oligomers compared to the comparators are presented in Table 3.

TABLE 3

Leaching of UV stabilisers based on NMR analysis.

| | | % leaching[d] | | | |
|---|---|---|---|---|---|
| Entry | SOC/oligomer | $H_2O$ | 15% EtOH | 3% AcOH | 95% EtOH[c] |
| 1 | O1 | 0 | <1 | 0 | 17 ± 2 |
| 2 | CA1 | 0 | <1 | 0 | 33 |
| 3 | O2[a] | 0 | <1 | 0 | 7 ± 2 |
| 4 | CA 2[b] | <1 | <1 | 0 | 35 |
| 5 | O3 | 0 | <1 | 0 | 11 ± 2 |
| 6 | CA3 | 0 | <1 | 0 | 48 |
| 7 | O4 | 0 | 0 | 0 | 7 ± 1 |
| 8 | CA4 | <1 | 2 | <1 | 46 |
| 9 | DHBP[a] | 2 | 8 | 1 | 77 |
| 10 | DHOBP[a] | 0 | 0 | 0 | 70 |
| 11 | BTAC[a] | 0 | 0 | 0 | 44 ± 1 |
| 12 | Uvinul 3030 | 0 | 0 | 0 | 10 ± 2 |

[a]quantified by ¹H NMR using mesitylene as an internal standard.
[b]quantified using UV calibration curve.
[c]Average % of three experiments.
[d]The % of leaching is based on the amount UV stabilizers (25 mg) incorporated in to PS (500 mg).

The results are also illustrated in FIGS. 8 to 11.

Applicability The disclosed group of bio-derived oligomeric materials that have potential ability to block the UV light in a wider spectrum (400-200 nm) and supported by detailed experimental studies. A green polymerization method was adopted to obtain the materials from natural feedstocks. The bio-derived oligomers possess number average molecular weights in the range 1100-2800 Da, which is appropriate for convenient blending with polymers. The photostability and UV blocking ability of the new bio-derived oligomers are comparable to some of the widely used synthetic UV stabilizers currently in the market.

The invention claimed is:

1. An oligomer of Formula (I):

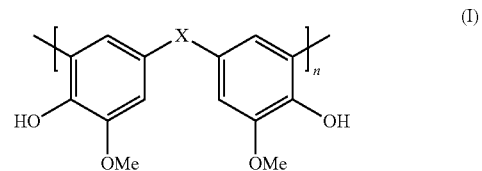

wherein X is selected from a heteroatom, $C_1$-$C_8$ acyclic, cyclic or heterocyclic linker; and n is an integer selected from 2 to 15;

wherein the oligomer does not contain a metal impurity.

2. The oligomer of claim 1, wherein X is a $C_4$-$C_8$ acyclic, cyclic or heterocyclic linker.

3. The oligomer of claim 1, wherein X is selected from

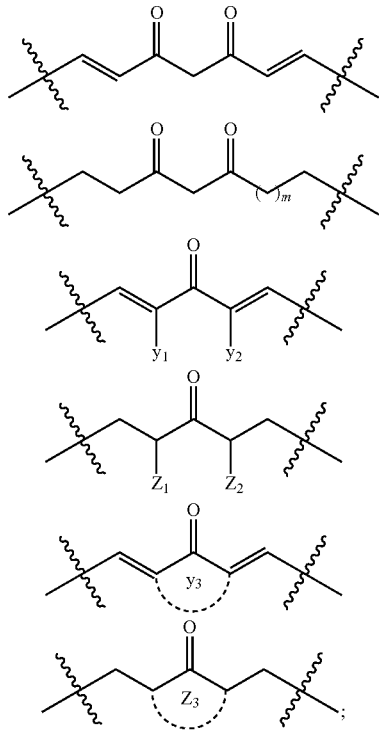

wherein m is an integer selected from 0 to 5;
$Y_1$, $Y_2$, $Z_1$ and $Z_2$ are independently H or $C_1$-$C_5$ alkyl; and
$Y_3$ and $Z_3$ are independently $C_4$-$C_6$ cycloalkyl.

4. The oligomer according to claim 1, wherein X is selected from

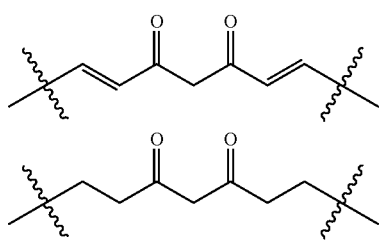

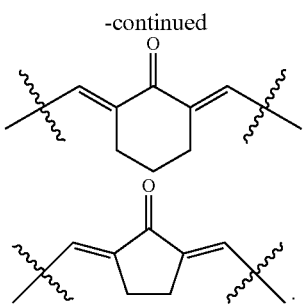

5. The oligomer according to claim 1, wherein n is an integer selected from 3 to 8.

6. The oligomer according to claim 1, having a number average molecular weight of about 1000 Da to about 3000 Da.

7. The oligomer according to claim 1, having a UV absorption within the range of about 200 nm to about 500 nm.

8. The oligomer according to claim 1, having a molar extinction coefficient of more than 30,000 M$^{-1}$ cm$^{-1}$.

9. A method of forming an oligomer, the method including the step of:
a) providing a monomer of Formula (II)

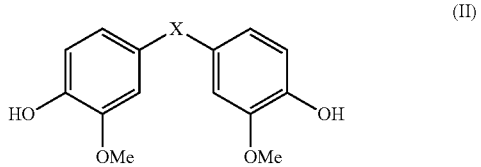

(II)

wherein X is selected from a heteroatom, $C_1$-$C_8$ acyclic, cyclic or heterocyclic linker; and
b) polymerising the monomer to form an oligomer of Formula (I);

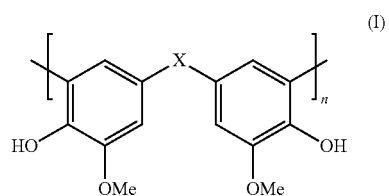

(I)

wherein the polymerising step comprises forming a C—C bond on the hydroxyphenyl ring of Formula (II);
wherein the polymerizing step is catalysed by an enzyme.

10. The method of claim 9, wherein the C—C bond is formed at an ortho position on the hydroxyphenyl ring of Formula (II).

11. The method according to claim 9, wherein the polymerising step is catalysed by laccase.

12. The method according to claim 9, wherein the polymerising step is performed in a solvent mixture, the solvent mixture comprising an aqueous solvent and another solvent, the combination of which results in a final single phase.

13. The method according to claim 9, wherein the monomer of Formula (II) is selected from:

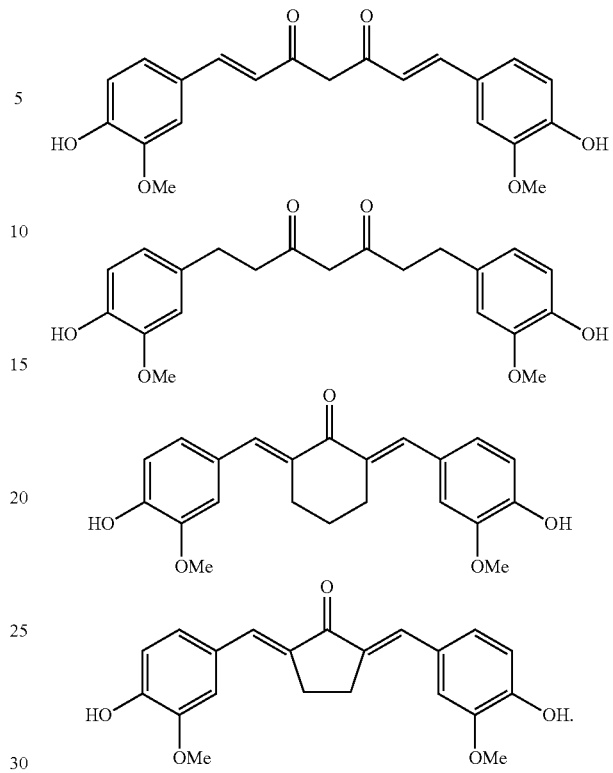

14. A composite, comprising:
a) an oligomer of Formula (I)

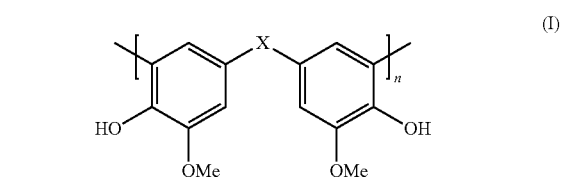

(I)

wherein X is selected from a heteroatom, $C_1$-$C_8$ acyclic, cyclic or heterocyclic linker; and
n is an integer selected from 2 to 15; and
b) a polymer matrix.

15. The composite of claim 14, wherein the polymer matrix is selected from polyvinyl chloride (PVC) or polystyrene (PS).

16. The composite of claim 14, wherein the oligomer of Formula (I) is present from about 1 wt/wt % to about 10 wt/wt %.

17. The composite according to claim 14, having a transmittance of more than 90% at about 400 nm to about 800 nm.

18. The composite according to claim 14, having a degradation of less than 20% after exposure to UV light for 120 h.

19. The composite according to claim 14, having a leaching rate in 95% ethanol of less than 20%.

20. The composite according to claim 14, wherein the composite does not contain a metal impurity.

* * * * *